US009968870B2

(12) United States Patent
Abeskaron et al.

(10) Patent No.: US 9,968,870 B2
(45) Date of Patent: May 15, 2018

(54) CELL WASHING DEVICE USING A BULK ACOUSTIC WAVE WITH PHANTOM MATERIAL

(71) Applicant: Biomet Biologics, LLC, Warsaw, IN (US)

(72) Inventors: David Abeskaron, Warsaw, IN (US); Michael D. Leach, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 224 days.

(21) Appl. No.: 14/978,417

(22) Filed: Dec. 22, 2015

(65) Prior Publication Data
US 2016/0175742 A1 Jun. 23, 2016

Related U.S. Application Data

(60) Provisional application No. 62/095,480, filed on Dec. 22, 2014.

(51) Int. Cl.
C02F 1/46 (2006.01)
B01D 21/28 (2006.01)
(Continued)

(52) U.S. Cl.
CPC ......... B01D 21/283 (2013.01); A61M 1/3678 (2014.02); A61M 1/3692 (2014.02); B03B 5/00 (2013.01); A61M 2202/0429 (2013.01)

(58) Field of Classification Search
CPC ...... B01D 29/115; B01D 37/00; B01D 29/52; B01D 29/865; B01D 2201/0415;
(Continued)

(56) References Cited

U.S. PATENT DOCUMENTS 5,225,089 A 7/1993 Benes et al.
5,367,127 A 11/1994 Dormon
(Continued)

FOREIGN PATENT DOCUMENTS

WO WO-9501214 A1 1/1995
WO WO-02072234 A1 9/2002
(Continued)

OTHER PUBLICATIONS

"International Application Serial No. PCT/US2015/067380, International Search Report dated Apr. 15, 2016", 5 pgs.
(Continued)

*Primary Examiner* — Walter D. Griffin
*Assistant Examiner* — Cameron J Allen
(74) *Attorney, Agent, or Firm* — Schwegman Lundberg & Woessner, P.A.

(57) ABSTRACT

Separation devices for separating a component from a multicomponent mixture are provided. The separation devices can include a body that defines a separation channel with a cross-sectional geometry that is not circular, rectangular, or square. The separation devices can be positioned relative to a base having an acoustic wave generator. A standing bulk acoustic wave generated by the acoustic wave generator can separate one or more components from the multicomponent mixture. Methods are provided for separating one or more components from a multicomponent mixture using the separation devices.

20 Claims, 6 Drawing Sheets

(51) Int. Cl.
*B03B 5/00* (2006.01)
*A61M 1/36* (2006.01)

(58) Field of Classification Search
CPC ...... B01D 2201/0446; B01D 2201/127; B01D 3/00; C02F 1/36; C02F 1/46
See application file for complete search history.

(56) References Cited

U.S. PATENT DOCUMENTS

| | | | |
|---|---|---|---|
| 5,803,270 A | 9/1998 | Brodeur | |
| 2006/0037915 A1* | 2/2006 | Strand | B01D 21/283 210/748.05 |
| 2009/0029870 A1* | 1/2009 | Ward | G01N 15/1404 506/9 |
| 2010/0137163 A1* | 6/2010 | Link | B01F 13/0071 506/16 |
| 2013/0026108 A1* | 1/2013 | Yager | C02F 1/36 210/748.04 |
| 2014/0008307 A1* | 1/2014 | Guldiken | B01L 3/502761 210/748.05 |

FOREIGN PATENT DOCUMENTS

| | | |
|---|---|---|
| WO | WO-2013049623 A1 | 4/2013 |
| WO | WO-2014138739 A1 | 9/2014 |
| WO | WO-2016106318 A1 | 6/2016 |

OTHER PUBLICATIONS

"International Application Serial No. PCT/US2015/067380, Written Opinion dated Apr. 15, 2016", 7 pgs.
1 "International Application U.S. Appl. No. PCT/US2015/067380, International Preliminary Report Ion Patentability mailed 07-06-17", 9 p_gs.

* cited by examiner

CELL WASHING DEVICE USING A BULK ACOUSTIC WAVE WITH PHANTOM MATERIAL

CLAIM OF PRIORITY

This patent application claims the benefit of priority of David Abeskaron, et al., U.S. Provisional Patent Application Ser. No. 62/095,480, entitled "CELL WASHING DEVICE USING A BULK ACOUSTIC WAVE WITH PHANTOM MATERIAL," filed on Dec. 22, 2014, which is hereby incorporated by reference herein in its entirety.

FIELD

This disclosure relates to devices and methods for separating components from a mixture (including a suspension), and particularly to separating a selected component from a mixture using a bulk acoustic wave to generate a separated component in a high concentration and purity.

BACKGROUND

Blood transfusions are used to treat many disorders and injuries, such as in the treatment of accident victims and during surgical procedures. According to current American Red Cross statistics, about 5 million people receive blood transfusions each year, in the United States alone. Thus, health care systems rely on the collection and distribution of blood. Typically, blood is obtained from a donor and then processed and stored; units of stored blood or blood products are then taken from storage as needed and transfused into a patient in need. In some cases, the blood may be an autologous donation, where an individual donates blood in expectation of receiving his or her own blood by transfusion during a medical procedure.

Donated blood is typically processed into components and then placed in storage until needed. When a subject is in need of a blood transfusion, a unit of blood is commonly removed from storage, rejuvenated, washed, and re-suspended in an appropriate solution. In some instances, the red blood cells were lyophilized prior to storage, in which case they need to be re-suspended, washed, and then re-suspended again in an appropriate solution. The re-suspended red blood cells are then transfused into the subject. In either scenario, washing the red blood cells is traditionally a tedious, time consuming and multistep process that requires a great deal of tubing, and the use of expensive centrifuges with rotating seals to separate the cells from the wash solution. Therefore, there remains a need to streamline and simplify the process for washing red blood cells prior to transfusion.

OVERVIEW

This section provides a general summary of the disclosure, and is not a comprehensive disclosure of its full scope or all of its features.

The present technology provides a separation device for separating at least one component from a multicomponent mixture. The device can include a first surface and a second surface, generally opposing the first surface. The body can define a separation channel extending between a first end and a second end. The separation channel can have a non-circular, non-square, and nonrectangular cross-sectional shape transverse to a longitudinal axis of the separation channel. The cross-sectional shape can be a triangle, a triangle with rounded corners, a tear-drop shape, or a pinched triangle or tear-drop shape. In various examples, the separation channel can have a triangular cross-sectional shape. In certain examples, the separation channel can define a plurality of isolation channels, such as two, three, four or more isolation channels. In one example, a separation channel can include three triangular isolation channels having triangular cross-sectional shapes transverse to the longitudinal axis, and a central isolation channel that is arranged centrally to the three triangular isolation channels. The central isolation channel can have a hexagonal cross-sectional shape. The first surface of the device can include a material that is configured to reflect an acoustic wave.

The present technology also provides a separation system for separating at least one component from a multicomponent mixture. The system can include a separation device that has a body with a first surface and a second opposing surface. The body can define a separation channel extending between a first end and a second end. The separation channel can have a non-circular, non-square, and non-rectangular cross-sectional shape transverse to a longitudinal axis of the separation channel. The cross-sectional shape can be a triangle, a triangle with rounded corners, a tear-drop shape, a pinched triangle or tear-drop shape, or other shape configured to have distinct separation areas. In various examples, the separation channel can have a triangular cross-sectional shape. In some examples, about midway through the separation channel, the separation channel can define a plurality of isolation channels, such as two, three, four or more isolation channels. In an example the isolation channels can include three triangular isolation channels having triangular cross-sectional shapes, and one central isolation channel that is central to the three triangular isolation channels. In some examples, a central isolation channel can have a hexagonal cross-sectional shape. The first surface of the device can include a material that can reflect an acoustic wave. The separation system can also include a base having an acoustic wave generator. The separation device can be positioned relative to the base such that the separation channel is positioned between an acoustic wave generator and the reflective material.

Additionally, the present technology provides a method for separating at least one component from a multicomponent mixture. The method can include mixing a first solution comprising at least one component with a second solution to form a multicomponent mixture, and delivering the multicomponent mixture through a separation channel of a separation device. The separation device can have a body with a first surface including a reflective material, layer, or film, and a second surface, generally opposing the first surface, the body defining a separation channel extending between a first end and a second end of the separation channel. In various examples, the first and second surfaces are generally planar top and bottom surfaces or opposing side surfaces. The separation channel can have a non-circular, non-square, and non-rectangular cross-sectional shape transverse to a longitudinal axis of the separation channel. The cross-sectional shape can be a triangle, a triangle with rounded corners, a tear-drop shape, a pinched triangle or tear-drop shape, or other shape designed to have distinct separation areas. In various examples, the separation channel can define a plurality of isolation channels, such as two, three, four or more isolation channels. In an example, a separation channel can have a triangular cross-sectional shape, and about midway through the separation channel the separation channel can define four isolation channels. The four isolation channels can include three triangular isolation channels having triangular cross-sectional shapes, and one central isolation channel that is arranged centrally to the three triangular isolation channels. In another example, the central isolation channel can have a hexagonal cross-sectional shape. The method can also include flowing the multicomponent mixture relative to a standing bulk acoustic wave to thereby separate the component from the multicomponent mixture; and collecting the component at an outlet at or adjacent to the second end of the device.

To further illustrate the devices and related method disclosed herein, a non-limiting list of examples provided here:

In Example 1, a separation device comprises a body having a first surface and a second surface, generally opposing the first surface, the body defining a separation channel extending between a first end and a second end, the separation channel having a non-circular cross-sectional geometry transverse to a longitudinal axis of the separation channel.

In Example 2, the separation device of Example 1 can optionally be configured such that the first surface comprises a reflective material configured to reflect an acoustic wave.

In Example 3, the separation device of Examples 1 and/or 2 can optionally be configured such that the reflective material comprises a glass, a plastic, a metal, a ceramic, or a combination thereof.

In Example 4, the separation device of any one or any combination of Examples 1-3 can optionally be configured such that the body comprises a phantom material that is configured to mimic an acoustical property of water.

In Example 5, the separation device of any one or any combination of Examples 1-4 can optionally be configured such that a pressure node of a standing bulk acoustic wave is located within the separation channel when the separation channel is positioned relative to an interdigitated transducer (IDT).

In Example 6, the separation device of any one or any combination of Examples 1-5 can optionally be configured such that the noncircular cross-sectional geometry of the separation channel is a triangle, a triangle with rounded corners, a tear-drop shape, or a pinched tear-drop shape.

In Example 7, the separation device of any one or any combination of Examples 1-6 can optionally be configured such that the noncircular cross-sectional geometry is a triangle.

In Example 8, the separation device of any one or any combination of Examples 1-7 can optionally be configured such that an apex of the separation channel is adjacent to the first surface and a base of the separation channel is adjacent to the second surface.

In Example 9, the separation device of any one or any combination of Examples 1-8 can optionally be configured such that about midway between the first end and the second end the separation channel defines three isolation channels having triangular cross-sectional geometries, each of the three isolation channels positioned along a different corner or side of the separation channel.

In Example 10, separation system for separating at least one component from a multicomponent mixture can include a separation device of any one or any combination of Examples 1-9, a reflective material, and a base unit comprising an acoustic wave generator, wherein in an assembled configuration the reflective material is positioned on the first surface and the separation device is mounted on the base unit such that the separation channel is positioned between the acoustic wave generator and the reflective material.

In Example 11, a separation system can include a separation device comprising a body having a first surface and a second surface, generally opposing the first surface, the body defining a separation channel extending between a first end and a second end, wherein the separation channel has a triangular cross-sectional geometry transverse to a longitudinal axis of the separation channel; a reflective material; and a base comprising an interdigitated transducer (IDT), wherein in an assembled configuration the reflective material is positioned on the first surface and the separation device is positioned relative to the base such that the separation channel is positioned between the IDT and the reflective material.

In Example 12, the separation system of Examples 10 and/or 11 can optionally be configured such that the separation device comprises a phantom material configured to mimic an acoustic property of a tissue.

In Example 13, the separation system of any one or any combination of Examples 10-12 can optionally be configured such that the reflective material comprises a glass, a plastic, a metal, a ceramic, or a combination thereof.

In Example 14, the separation system of any one or any combination of Examples 10-13 can optionally be configured such that the base comprises a piezoelectric material.

In Example 15, the separation system of any one or any combination of Examples 10-14 can optionally be configured such that the separation device further comprises an inlet adjacent to the first end and an outlet adjacent to the second end.

In Example 16, the separation system of any one or any combination of Examples 10-15 can optionally be configured such that a triangular cross-sectional geometry is a triangle with rounded corners.

In Example 17, the separation system of any one or any combination of Examples 10-16 can optionally be configured such that the separation channel comprises a separation region and the separation device is positioned relative to the base such that the separation region is positioned between the reflective material and the IDT.

In Example 18, the separation system of any one or any combination of Examples 10-17 can optionally be configured such that the separation channel has a cross-sectional size that increases between the first end and the second end.

In Example 19, the separation system of any one or any combination of Examples 10-18 can optionally be configured such that when a standing bulk acoustic wave is generated between the IDT and the reflective material, a pressure node is located within the separation channel.

In Example 20, the separation system of any one or any combination of Examples 10-19 can optionally be configured such that about midway through the separation channel the separation channel defines three isolation channels having triangular cross-sectional geometries, each of the three isolation channels positioned along a different corner or side of the separation channel.

In Example 21, the separation system of any one or any combination of Examples 10-20 can optionally be configured such that the isolation channels do not contact each other.

In Example 22, the separation system of any one or any combination of Examples 10-21 can optionally be configured such that the base comprises a plurality of aligned IDTs, and the separation device is positioned relative to the base unit such that the aligned IDTs are aligned with the separation channel.

In Example 23, the separation system of any one or any combination of Examples 10-22 can optionally be configured such that the separation channel, the isolation channels, or both, increase in size in a direction from the first end to the second end.

In Example 24, a method for separating a component from a multicomponent mixture can comprise: delivering a multicomponent mixture through a separation channel of a separation device of any one or any combination of Examples 1-23, generating a standing bulk acoustic wave in the separation device; separating at least one component from the multicomponent mixture by flowing the multicomponent mixture relative to the standing bulk acoustic wave, between the first end and the second end; and collecting the component at an outlet adjacent to the second end.

In Example 25, a method for separating at least one component from a multicomponent mixture can comprise: delivering a multicomponent mixture through a separation channel of a separation device, the separation device having a first surface including a reflective material configured to reflect an acoustic wave, and a second surface, generally opposing the first surface, the separation device defining a separation channel extending between a first end and a second end, the separation channel having a non-circular cross-sectional geometry transverse to a longitudinal axis of the separation channel; generating a standing bulk acoustic wave; separating a component from the multicomponent mixture by flowing the multicomponent mixture relative to the standing bulk acoustic wave, between the first end and the second end; and collecting the component at an outlet adjacent to the second end.

In Example 26, the method of Example 24 and/or 25 can optionally be modified such that delivering includes mixing a first solution comprising the at least one component with a second solution to form the multicomponent mixture.

In Example 27, the method of any one or any combination of Examples 24-26 can optionally be modified to include mixing a first solution with a second solution prior to and outside of the separation device, or within the separation channel adjacent the first end.

In Example 28, the method of any one or any combination of Examples 24-27 can optionally be modified to include mounting the separation device on a base unit comprising an interdigitated transducer (IDT), such that the separation channel is positioned between the IDT and the reflective material.

In Example 29, the method of any one or any combination of Examples 24-28 can optionally be modified to include using a pressure node of the standing bulk acoustic wave to separate the at least one component from the multicomponent mixture.

In Example 30, the method of any one or any combination of Examples 24-29 can optionally be modified such that the non-circular cross-sectional geometry of the separation channel is a triangle, a triangle with rounded corners, a tear-drop shape, or a pinched tear-drop shape.

In Example 31, the method of any one or any combination of Examples 24-30 can optionally be modified such that the non-circular cross-sectional geometry of the separation channel is a triangle and separating includes using a pressure node to force the at least one component to an upper corner of the separation channel.

In Example 32, the method of any one or any combination of Examples 24-31 can optionally be modified such that the at least one component comprises red blood cells and the second solution comprises a wash solution.

In Example 33, the method of any one or any combination of Examples 24-32 can optionally be modified such that the separation channel comprises a triangular cross-sectional geometry, and wherein about midway between the first end and the second end the separation channel defines three triangular isolation channels having triangular cross-sectional geometries, positioned along different corners or sides of the separation channel and not in contact with one another, and one central isolation channel positioned central to the three triangular isolation channels.

In Example 34, the method of any one or any combination of Examples 24-33 can optionally be modified such that the at least one component comprises three components and separating includes separating the three components into the three triangular isolation channels.

In Example 35, the method of any one or any combination of Examples 24-34 can optionally be modified such that the multicomponent mixture comprises red blood cells, white blood cells, platelets, or a combination thereof.

In Example 36, the method of any one or any combination of Examples 24-35 can optionally be modified to include isolating a wash solution from the at least one component.

In Example 37, the method of any one or any combination of Examples 24-35 can optionally modified such that the method comprises any one or any combination of the devices or systems of Examples 1-23.

In Example 38, the separation device, separation system and related method of any one (or portion of any one) or any combination of Examples 1-36 can optionally be configured such that all elements or options recited are available to use or select from.

Further areas of applicability will become apparent from the description provided herein. This overview is intended to provide an overview of the subject matter of the present patent application. It is not intended to provide an exclusive or exhaustive explanation of the invention. The description and specific examples in this summary are intended for purposes of illustration only and are not intended to limit the scope of the present disclosure. The detailed description is included to provide further information about the present patent application.

BRIEF DESCRIPTION OF THE DRAWINGS

In the drawings, which are not necessarily drawn to scale, like numerals may describe similar components in different views. Like numerals having different letter or other suffixes may represent different instances of similar components. The drawings illustrate generally, by way of example, but not by way of limitation, various examples and combinations discussed in the present document. The drawings do not encompass all possible examples, combinations or implementations, and are not intended to limit the scope of the present disclosure.

DETAILED DESCRIPTION

Example embodiments will now be described more fully with reference to the accompanying drawings.

Although traditional methods for washing blood are effective, there remains a need to streamline the process for processing and washing blood. One possibility of streamlining the processes for processing and washing blood includes the use of standing waves, also referred to as stationary waves. Generally, standing waves can be formed from various mechanics, including interference between two waves. For example, two opposing waves can move towards one another in a medium and cause the formation of a standing wave. When two waves are generated on opposite ends of a medium, they can interfere with each other to generate a standing bulk acoustic wave (SBAW). Like other stationary waves, SBAWs are associated with both air displacement and pressure variation. Pressure variation can be used to manipulate particles in solution. Therefore, devices and methods for separating a component from a mixture with the use of SBAWs can be used to streamline processes for processing multicomponent mixtures.

The present technology provides devices, systems, and methods for separating at least one component from a multicomponent mixture. The device, system, and methods include the use of standing bulk acoustic waves (SBAWs) that can generate pressure nodes in a separation channel of a separation device. SBAWs result when acoustic waves constructively interfere with each other in opposing directions. For example, acoustic wave generators positioned on opposite sides of a piezoelectric material can generate SBAWs. A pressure node of an SBAW can force, move, or push a component in a mixture to a location within a separation channel based on the component's acoustical, physical, and mechanical properties.

Figures 1A, 1B:
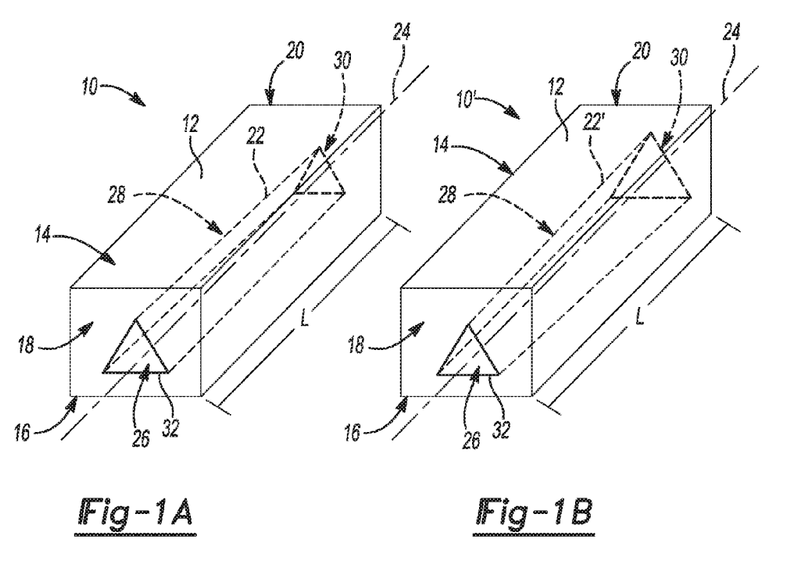
FIG. 1A illustrates a separation device having a separation channel according an example.
FIG. 1B illustrates a separation device having a separation channel according to an example.

With reference to FIG. 1A, the present technology provides a device 10 for separating at least one component 110 from a multicomponent mixture 400. The device 10 can have a body 12 that includes a first surface 14, and a second surface 16, generally opposed to the first surface. In various embodiments, the first surface 14 and the second surface 16 can be top and bottom surfaces or opposing side surfaces. In some embodiments, the first surface 14 and the second surface 16 can be generally planar surfaces. The body 12 can define a separation channel 22 extending a length L along a longitudinal axis 24 between a first end 18 and a second end 20. In some examples, the length L of the separation channel 22 can extend substantially the length of the body 12. In other examples, the separation channel 22 can extend a length L that is less than the entire length of the body 12. The separation channel 22 can have an inlet 26, a separation portion 28, and an outlet 30. As shown in FIG. 1A, the separation channel 22 of device 10 can have a constant cross-sectional size between the first end 18 and the second end 20. However, in various examples, the cross-sectional size, the cross-section shape, or both, of the separation channel 22 can change. For example, FIG. 1B shows a device 10' that shares many of the features of device 10. However, device 10' comprises a separation channel 22' with a cross-sectional size that increases in size between the first end 18 and the second end 20. The increase of separation channel size between one end and another is referred to as "draft" herein. The draft can be small, such as from about 1 to about 4 mm, or the draft can be large, such as from about 5 to about 10 mm or greater than about 10 mm. The size of the draft can depend on at least one of a length of the separation channel 22' or the cross-sectional size, dimensions, and/or area of the separation channel 22'. For example, the device 10, 10' can have a separation channel 22, 22' with a length from about 5 cm to about 20 cm, or longer than about 20 cm depending on the volume of a mixture that needs to be processed by the device 10, 10'. In some embodiments, the length L of the separation channel 22, 22' of device 10, 10' can be from about 5 cm to about 15 cm or from about 5 cm to about 10 cm.

Figure 2A:
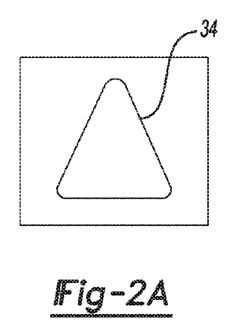
FIG. 2A illustrates of cross-sectional view of a separation channel according to an example.
Figure 2B:
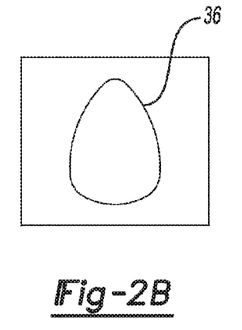
FIG. 2B illustrates a cross-sectional view of a separation channel according to an example.
Figure 2C:
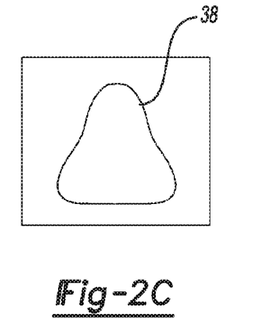
FIG. 2C illustrates a cross-sectional view of a separation channel according to an example.

As shown in FIGS. 1A and 1B, the separation channel 22, 22' can have a cross sectional geometry G that is not circular, rectangular or square. Rather, the cross-sectional geometry G can be designed to have distinct separation areas. In certain examples, the device 10, 10' can have a separation channel 22, 22' that can have a generally triangular cross-sectional geometry G such that a corner or an apex A of the separation channel points to the first surface 14 and a side, edge or base B of the separation channel faces the second surface 16. Although the separation channel 22, 22' in FIGS. 1A and 1B can have a cross-sectional geometry G of equilateral triangles 32, the cross-sectional geometry can be equilateral, isosceles, or scalene triangles. In various embodiments, the separation channel 22, 22', e.g., a triangle can have an apex adjacent to the first surface 14 and a base adjacent to the second surface 16. Moreover, in various embodiments a separation channel 22, 22' can have a cross-sectional geometry G that is not a perfect geometry, e.g., not a perfect triangle, as shown in FIGS. 2A, 2B, and 2C. Specifically, FIG. 2A shows a cross-sectional geometry of a triangle with rounded corners 34, FIG. 2B shows a cross-sectional geometry that has a shape of a tear-drop 36, and FIG. 2C shows a cross-sectional geometry that has a shape of a pinched triangle or triangle or tear-drop 38. Nonetheless, a separation channel 22, 22' of the present technology can have any non-circular, non-square, and non-rectangular cross-sectional geometries, other than those shown in the figures, so long as the cross-sectional geometries of the separation channel provide distinct separation areas. The distinct separation areas can efficiently guide isolated components through the separation channel with minimal aggregation.

Figure 3A:
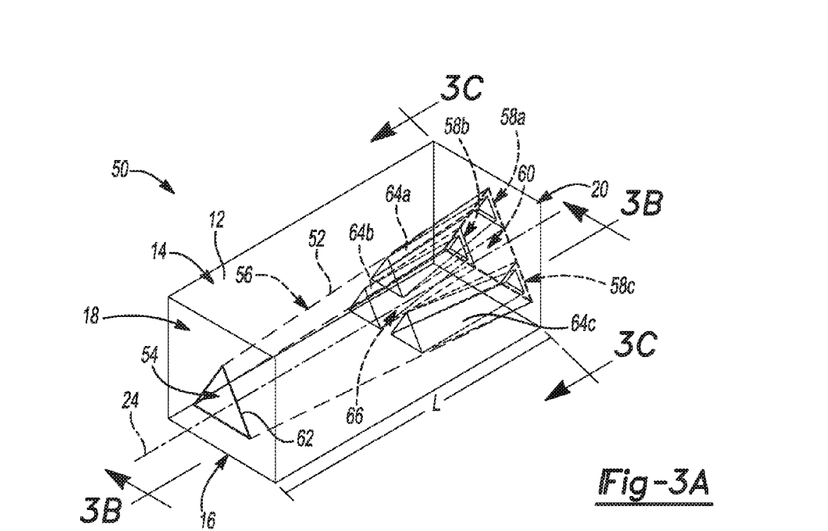
FIG. 3A illustrates a separation device having a separation channel with a plurality of isolation channels according to an example.
Figures 3B, 3C:
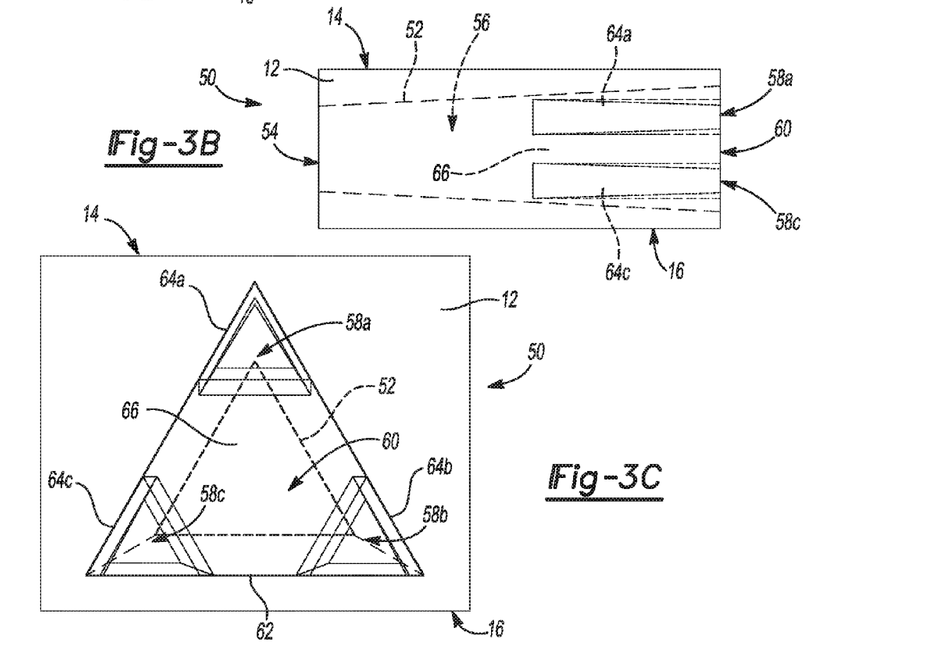
FIG. 3B illustrates a cross-sectional view of an example of a separation device according to FIG. 3A, taken along line 3B.
FIG. 3C illustrates a cross-sectional view of a separation device according to FIG. 3A, taken along line 3C.

FIGS. 3A-3C show an exemplary separation device 50 similar to the device 10' of FIG. 1B. Like the device 10' of FIG. 1B, the device 50 of FIGS. 3A-3B can include a body 12 comprising a first surface 14, and a second surface 16 generally opposing the first surface. Although the first surface 14 and second surface 16 can be generally opposing top and bottom surfaces, as shown in FIG. 3A; in other examples, the first surface 14 and second surface 16 can be generally opposing side surfaces. In some examples, the first surface 14 and second surface 16 can be generally planar surfaces. The body 12 can define a separation channel 52 extending a length L along a longitudinal axis 24 between a first end 18 and a second end 20. In some examples, the length L of the separation channel extends substantially the entire length of the body 12. In other examples, the separation channel 22 can extend a length L that is less than the entire length of the body 12. The separation channel 52 can have at least one inlet 54, a separation portion or isolation region 56, and at least one outlet 58. In some examples, the at least one outlet 58 can comprise a plurality of outlets, such as two, three, four, or more outlets. In certain examples, the at least one outlet comprises first, second, and third outlets 58a, 58b, 58c. In some examples, first, second and third outlets 58a, 58b, 58c can each have a triangular cross-sectional geometry. In certain examples, the at least one outlet 58 can comprise a plurality of outlets positioned around a central outlet 60. In some examples, the central outlet 60 can have a hexagonal cross-sectional geometry. Although the device 50 is shown with a draft, in other examples, the device 50 can have a constant cross-sectional size between the first end 18 and the second end 20, i.e., can have no draft.

In an example, a separation channel 52 can have a triangular cross-sectional geometry 62. The separation channel 52 can define a plurality of isolation channels, such as two, three, four or more isolation channels 64, 66. In some examples, the isolation channels 64, 66 can have cross-sectional geometries or shapes, transverse to the longitudinal axis of the separation channel, that are the same or substantially the same as the cross-sectional shape of the separation channel 52. In other examples, the isolation channels 64, 66 can have a cross-sectional geometries of shapes that are different from the cross-sectional shape of the separation channel 52. In yet other examples, certain ones of the isolation channels 64, 66 can have a cross-sectional shape that is the same, or substantially the same, as the cross-sectional shape of the separation channel, while other ones of the isolation channels 64, 66 can have a cross-sectional shape that is different from the cross-sectional shape of the separation channel. In some examples, certain ones of the isolation channels 64 can be arranged near the periphery, walls or corners of the separation channel. In other examples, one or more isolation channels 66 may be arranged centrally to the separation channel, or centrally to other isolation channels, i.e., the central isolation channel can be surrounded, wholly or partially, by other isolation channels. In some examples, the isolation channel 64, 66 can extend substantially the entire length L of the separation channel 52 between the first end 18 and the second end 20. In other examples, the isolation channel 64 can extend only partially along the length L of the separation channel 52 between the first end 18 and the second end 20. In an example, about midway along the separation channel 52, or at about a distance of L/2 from the first end 18, the separation channel 52 can define distinct and separate first, second, and third isolation channels 64a, 64b, 64c. In some examples, the first, second and third isolation channels can have triangular cross-sectional geometries that extend to the second end 20 and can be in communication with first, second, and third outlets 58a, 58b, 58c, respectively, at or adjacent to the second end 20. In an example, the three triangular isolation channels 64a, 64b, 64c do not contact one another. In another example, the separation channel 52 can further define a central isolation channel 66 that is central to the three triangular isolation channels 64a, 64b, 64c, and that extends to the second end 20 and is in communication with a central outlet 60. In some examples, one or both of the central isolation channel 66 and central outlet 60 can have a hexagonal cross-sectional geometry. As shown in FIGS. 3A, 3B, and 3C, each of the three isolation channels 64a, 64b, 64c can be positioned along a different one of the three corners of the separation channel 52. In other examples, the three isolation channels 64a, 64b, 64c can be positioned along three different sides of the separation channel 52. In various examples, the separation channel 52 can define three triangular isolation channels 64a, 64b, 64c and a central isolation channel 66. In certain examples, one or more isolation channels 64a, 64b, 64c, 66 can commence at a distance from the first end 18 such that the isolation channel does not extend substantially the entire length L of the separation channel 52. In some examples the isolation channel 64a, 64b, 64c, 66 can commence at a distance of about L/3, about L/2 (midway), about L/1.5, or about L/1.33 from the first end 18. In examples where the isolation channel 64a, 64b, 64c, 66 does not extend substantially the entire length L of the separation channel 52, the separation channel 52 can further define a mixing region 53 adjacent to the first end 18. Additionally, although the corners of the separation channel 52 and the three triangular isolation channels 64a, 64b, 64c can all be pointed, in other examples, the cross sectional geometries can be triangles with curved corners.

The separation device 10, 10', 50 of the present technology can comprise a phantom material 300 that can mimic one or more acoustical, physical and mechanical properties of real biological tissues, or can have about the same water content of real biological tissues. In other examples, the phantom material 300 can mimic one or more acoustical properties of water. Phantom materials are well known and commercially available. For example, phantom material can be provided by Computerized Imagining Reference Systems, Inc. (Norfolk, Va.) for use as a phantom material 300 of the separation device 10, 10', 50. Other materials can be used in the separation devices 10, 10', 50 including plastics, polymers, and piezoelectric materials. The separation device 10, 10', 50 can be made by any technique commonly known or used in the art, such as, for example, injection molding, compression molding, or 3-dimensional printing (3-D printing).

Figure 4:
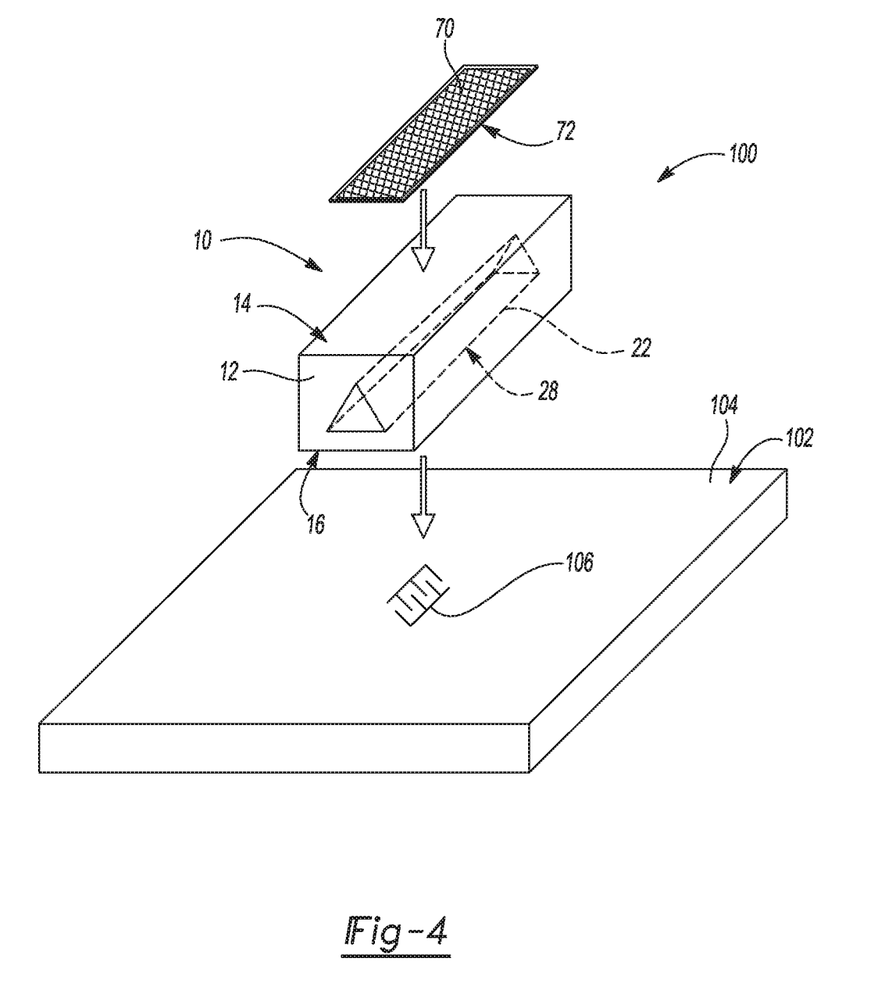
FIG. 4 illustrates an exploded view of a separation system according to an example.
Figures 5, 6:
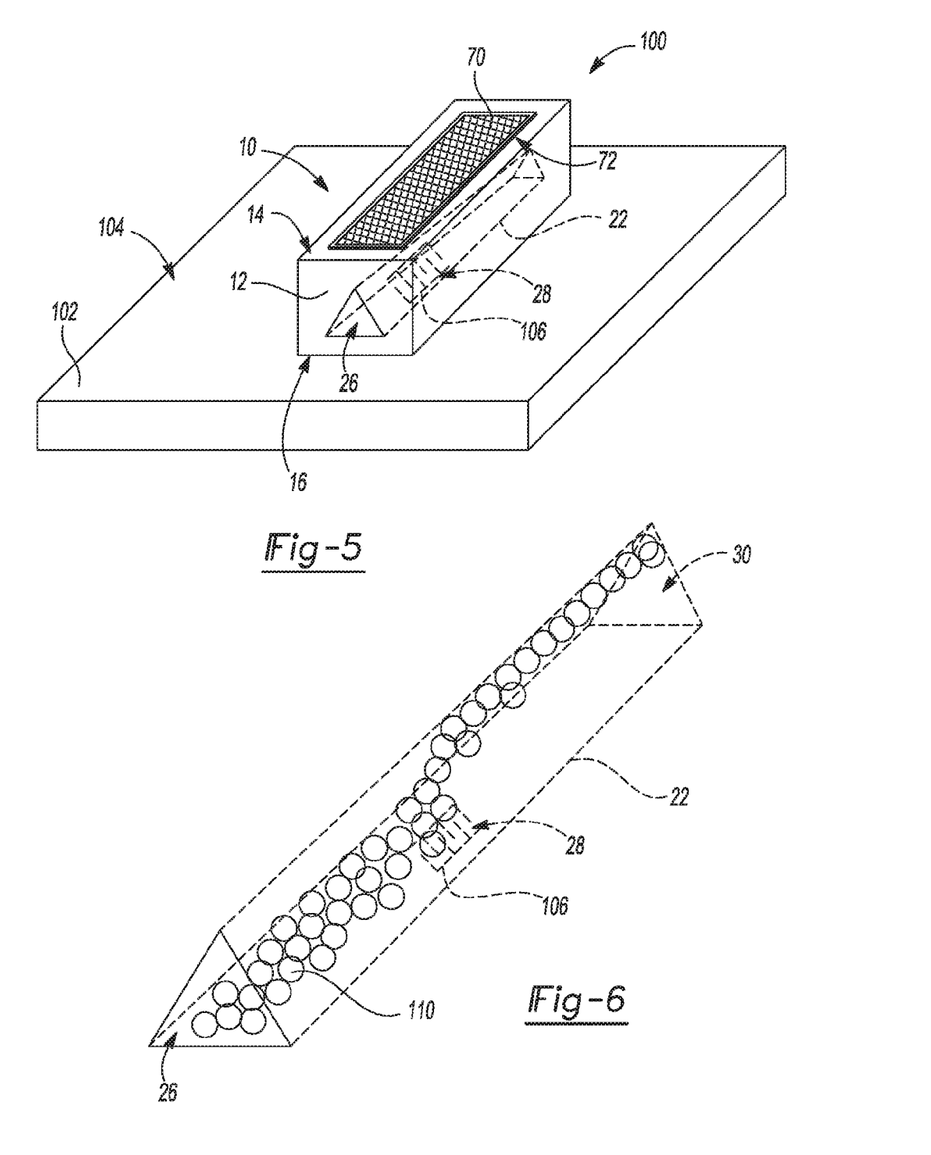
FIG. 5 illustrates a separation system including the separation device according to an example.
FIG. 6 illustrates a multicomponent mixture flowing through a separation channel according to an example, and a component being separated from the multicomponent mixture.
Figure 7:
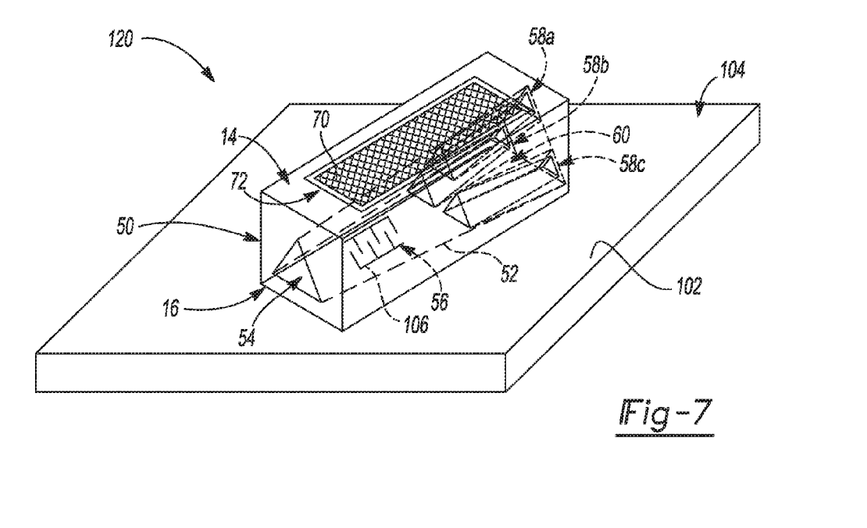
FIG. 7 illustrates a separation system including a separation device according to an example.

As discussed further below, and as shown in FIGS. 4, 5 and 7, the separation device 10, 10', 50 of the present technology can comprise a reflective material, layer, or film 70 that can be configured to be positioned on the first surface 14 of the separation device 10, 10', 50 to reflect an acoustic wave W. Therefore, the separation device 10, 10', 50 can comprise a reflective surface 72 when a reflective material, layer, or film 70 is positioned on the first surface 14. In various embodiments, the reflective material 70 or reflective surface 72 can be a planar slide or membrane comprising a glass, a polymer, a plastic, a metal, a ceramic, or a combination thereof. As non-limiting examples, the reflective material, layer or film 70 or reflective surface 72 can be biaxially-oriented polyethylene terephthalate (boPET) polyester film (such as Mylar® brand BoPET commercialized by DuPont; Wilmington, Del.), glass mica, polymers, or a combination thereof.

With reference to FIGS. 4 and 5, the present technology also provides a system 100 for separating at least one component 110 from a multicomponent mixture 400. In various embodiments, the at least one component can be red blood cells 122 and the multicomponent mixture 400 can comprise the red blood cells 122, at least one solution 402, and optionally other cell types, such as white blood cells 124 and platelets 126. For example, before transfusions, red blood cells are often rejuvenated with a rejuvenation solution, such as Rejuvesol® red blood cell processing solution commercialized by Citra Labs, LLC (Braintree, Mass.). After rejuvenation, rejuvenated red blood cells are washed with a wash solution, such as water, saline, dextrose, saline with 5% dextrose, phosphate buffered saline, and other wash liquids to remove excess rejuvenation solution from the red blood cells. Therefore, the rejuvenation solution and/or the wash solution are removed from the red blood cells. Accordingly, the system 100 can be used to separate red blood cells 122 from a multicomponent mixture 400 of red blood cells 122, rejuvenation solution or wash solution 402, or both, and optionally other types of cells, such as white blood cells 124, platelets 126, or a combination thereof.

The system 100 can comprise a separation device 10, 10', 50, such as any separation device described above. However, the separation device 10 shown in FIGS. 4 and 5 can be the same separation device 10 described above in regard to FIG. 1A or the devices shown in FIGS. 3A-3C. The system 100 can also comprise a reflective material, layer, or film 70 having a reflective surface 72 that is configured to be positioned on the first surface 14 of the separation device 10, 10', 50. As described above, in various embodiments, the reflective material 70, 72 can be a planar slide or membrane comprising a glass, a polymer, a plastic, a metal, a ceramic or a combination thereof. As non-limiting examples, the reflective material, layer, or film 70, 72 can be biaxially-oriented polyethylene terephthalate (boPET) polyester film (such as Mylar® brand BoPET commercialized by DuPont; Wilmington, Del.), glass mica, polymers, or a combination thereof. The system 100 can further comprise a base 102 that can include a surface 104 that can be configured to be positioned relative to the separation device, and an acoustic wave generator 106.

In various embodiments, the base 102 can comprise a piezoelectric material. Any piezoelectric material known in the art can be used in the base unit 102. Non-limiting examples of piezoelectric materials include quartz, quartz crystal, ceramic, ceramic composites, berlinite ($AlPO_4$), lead titanate ($PbTiO_3$), barium titanate ($BaTiO_3$), lead zirconate titanate ($Pb[Zr_xTi_{1-x}]O_3$, $0 \leq x \leq$; "PZT"), potassium niobate ($KNbO_3$), lithium niobate ($LiNbO_3$), lithium tantalate ($LiTaO_3$), sodium tungstate ($Na_2WO_3$), $Ba_2NaNb_5O_5$, $Pb_2KNb_5O_{15}$, zinc oxide (ZnO), sodium potassium niobate (($K,Na)NbO_3$), bismuth ferrite ($BiFeO_3$), sodium niobate ($NaNbO_3$), bismuth titanate ($Bi_4Ti_3O_{12}$, sodium bismuth titanate $Na_{0.5}Bi_{0.5}TiO_3$, and polymers, such as polyvinylidene fluoride (PVDF). The acoustic wave generator 106 can be any acoustic wave generator known or used in the art. As a non-limiting examples, the acoustic wave generator 106 can be a piezoelectric transducer, or an interdigitated transducer (IDT)

As depicted in FIGS. 4 and 5, in various examples of an assembled system 100, the reflective material 70, 72 can be configured to be positioned on the device 10, 10', 50 and the device 10, 10', 50 can be configured to be mounted on the base unit 102 such that the separation channel 22, 52 is generally positioned between, or directly between, the wave generator 106 and the reflective material, layer, or film 70. The wave generator 106 can generate an acoustic wave that passes through the body's 12, such as through the phantom material 300, and can be reflected back through itself by the reflective material, layer, or film 70 to generate an SBAW W. The SBAW W can pass through the separation channel 22, 52 such that a pressure node N is present within the separation channel 22, 52. In some embodiments, the separation region 28, 56 of the separation channel 22, 52 can be positioned directly between the wave generator 106 and the reflective material 70, 72 so that the pressure node N is located in the separation region 28, 56 of the separation channel 22, 52.

In certain examples, flow of the multicomponent mixture 400 through the separation channel 22, 52 can be established by at least one pump. In some examples, at least one component 110 can be mixed with a solution 402 in a mixing container outside of the system 100 to generate the multicomponent mixture 400, and the multicomponent mixture 400 can be introduced through the system by a single pump. In other embodiments, the component can be fed into a select one of the least one inlet 26 of the separation channel 22, for example by a first pump, and a solution can fed into a second one of the at least one inlet 26 of channel 22, for example by a second pump, such the multicomponent mixture is formed in a mixing region 53 of the separation channel 22 at or near the first end 18. The at least one pump can be any pump used in the art. As non-limiting examples, the pump can be a peristaltic pump, rotor-operated pump, pressure infusor (bag squeezer) or a combination thereof. In some embodiments, the pump can provide a steady and continuous flow rate with little or no variation. Therefore, pulses are kept at a minimum. Pulse dampeners, pulse suppressors, or baffles, can be used to eliminate pulses from pumps that generate pulsed flow. Suitable pumps, pulse dampeners, and pulse suppressors are described in U.S. patent application Ser. No. 14/519,302, filed on Oct. 21, 2014, to Hamman et al., which is incorporated herein by reference.

When a multicomponent mixture 400 is flowed through the separation channel 22 a pressure node N generated by the SBAW W forces, moves, or pushes a component 110 in the multicomponent mixture 400 to a location within the separation channel 22 based on an acoustical, physical, and/or mechanical property of the component. In some embodiments, the at least one component 110 can be red blood cells, as shown in FIG. 6. In FIG. 6, a multicomponent mixture 400 comprising red blood cells is introduced through the separation channel 22 at the inlet 26. When the red blood cells 110 interact with the pressure node N in the separation region 28 of the channel 22, the red blood cells are forced, moved, or pushed to a corner edge of the channel 22. By being forced, moved or pushed to the corner edge, the red blood cells are concentrated and separated from the rest of the multicomponent mixture 402, which can include a solution 402, such as rejuvenation solution and/or wash solution. The red blood cells 110 can then collected at the outlet 30 of the device 10.

Another example of a separation system 120 is shown in FIG. 7. The separation system 120 is similar to the system 100 of FIG. 5, except that the system 120 can include the separation device 50 described in FIGS. 6A, 6B, and 6C. Again, although the separation system 120 can include the separation device 50, any separation device described herein can be used in a separation system 120 provided by the present technology.

In FIG. 7, a reflective material, layer, or film 70, 72 can be provided to be positioned on the device 50, and the device 50 can be configured to be positioned relative to the base 102 such that the separation channel 52 is generally positioned between, or directly positioned between, the acoustic wave generator 106 and the reflective material, layer, or film 70, 72. The acoustic wave generator 106 can generate an acoustic wave that passes through the body's 12 e.g., through the body's phantom material 300, and is reflected back through itself by the reflective material, layer, or film 70, 72 to generate an SBAW W. The SBAW W passes through the separation channel 52 such that a pressure node N is present within the channel 52. In some embodiments, a separation region 56 of the separation channel 52 can be positioned directly between the wave generator 106 and the reflective material, layer, or film 70, 72 so that the pressure node N is located in the separation region 56 of the separation channel 52. Because different cell types react with pressure nodes differently, based on an individual cell's acoustical, physical, and/or mechanical properties, the separation system 120 can be used for isolating and separating multiple tissues or cellular components from a multicomponent mixture.

In some embodiments a separation system can comprise a base 102 including a plurality of acoustic wave generators 106 that are aligned with a separation channel 52 when a separation device 10, 50 is positioned relative to the base 102. Each wave generator 106 can generate an SBAW W with a plurality of pressure node N such that no two pressure nodes N are located in the same position within the separation channel 52. The different pressure nodes N can force, move, or push different ones of the at least one component 110 in a multicomponent mixture 400 to different, distinct locations in the separation channel 52.

Figure 8:
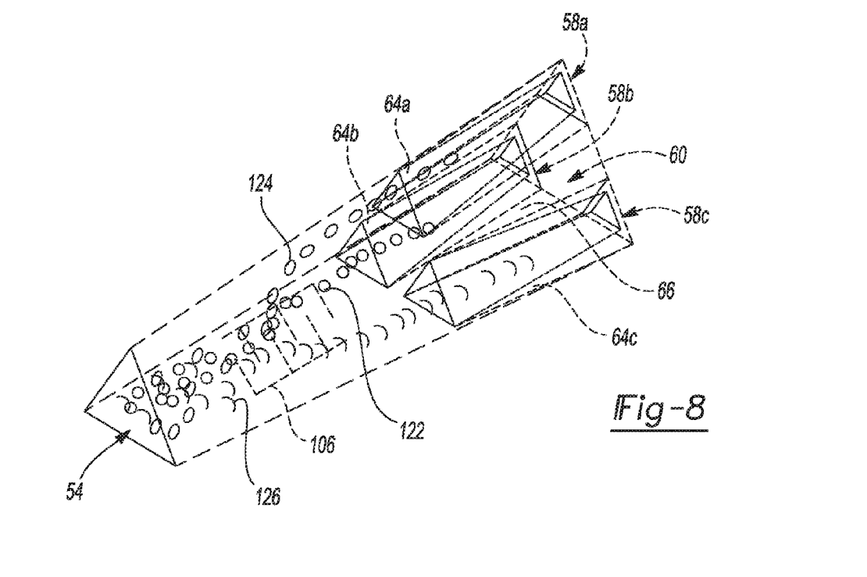
FIG. 8 illustrates a multicomponent mixture flowing through a separation channel that defines a plurality of isolation channels according to an example, and separation of a plurality of different components from the multicomponent mixture.

With reference to FIGS. 7 and 8, when a multicomponent mixture 400 flows through the separation channel 52, a pressure node N generated by the SBAW W can force, move, or push at least one component 110 in a multicomponent mixture 400 to a distinct location within the separation channel 52 based on the component's acoustical, physical, and/or mechanical properties. In some examples, the multicomponent mixture 400 can comprise a plurality of components 110, such as red blood cells 122, white blood cells 124, and platelets 126, as well as a solution 402, such as one or both of a rejuvenation solution and a wash solution. In FIG. 8, a multicomponent mixture 400 comprising red blood cells 122, white blood cells 124, and platelets 126 is introduced through the separation channel 52 via at least one inlet 54. When the red blood cells 122, white blood cells 124, and platelets 126 interact with a pressure node N in the separation region 56 of the separation channel 52, the red blood cells 122, white blood cells 124, and platelets 126 can be forced, moved, or pushed to different corners or edges of the separation channel 52. By being forced, moved or pushed to the different corners or edges of the separation channel, the red blood cells 122, white blood cells 124, and platelets 126 can be individually concentrated and separated from each other and from the rest of the multicomponent mixture, such as a solution 402, which can include rejuvenation solution and/or wash solution. The red blood cells 122, white blood cells 124, and platelets 126 can be forced, moved or pushed to the different corners or edges of the separation channel to enter, respectively, first, second, and third isolation channels 64a, 64b, 64c to further separate the cells from each other and from the rest of the multicomponent mixture, such as a solution 402. In some examples, the solution 402 can flow to a central channel 66. The red blood cells 122, white blood cells 124, and platelets 126 can collected at the first, second, and third outlets 58a, 58b, 58c, respectively, and the rest of the mixture, such as a solution 402, can be collected at a central outlet 60.

Figure 9:
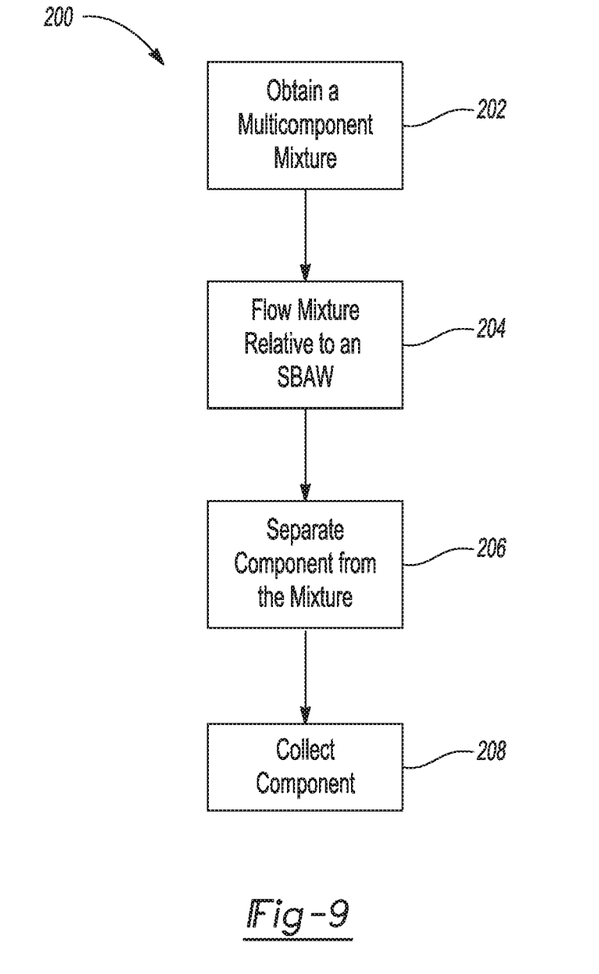
FIG. 9 illustrates a method of separating a component from a multicomponent mixture.

The present technology can also provide a method 200 for separating at least one component from a multicomponent mixture, as shown in FIG. 9. As shown in block 202, the method 200 can comprise obtaining a multicomponent mixture 400. Obtaining a multicomponent mixture 400 can include mixing a first solution S1 comprising the at least one component 110 with a second solution S2 to form the multicomponent mixture 400. The at least one component 110 can be any component that can be manipulated by a SBAW W due to one or more of the component's acoustical, physical, or mechanical properties. In various embodiments, the at least one component 110 can be red blood cells, white blood cells, platelets, or a combinations thereof. In some examples, the second solution S2 can be, for example, a rejuvenation solution, a wash solution, or both a rejuvenation solution and a wash solution.

As shown in block 204, the method 200 can comprise generating an SBAW W and delivering the multicomponent mixture 400 relative to the SBAW W, thereby separating the at least one component 110 from the remainder of the multicomponent mixture, such as a solution 402. Delivering the multicomponent mixture 400 relative to the SBAW comprises flowing or pumping the multicomponent mixture 400 through a separation channel 26, 52 of a separation device 10, 50, the separation device having a body 12 with a first surface 14, optionally including a reflective material 70,72, a second surface 16, opposing the first surface, the body defining a separation channel 22, 52 extending between a first end 18 and a second end 20, the separation channel 22, 52 having a non-circular cross-sectional geometry transverse to a longitudinal axis of the separation channel, wherein a pressure node N associated with the SBAW W is located within the separation channel 22, 52. The separation device can include any separation device described herein. In some embodiments, the method 200 can comprise mounting a separation device 10, 50 on a base unit 102 comprising an acoustic wave generator 106 such that a separation channel 22, 52 is positioned between the acoustic wave generator or IDT 106 and the reflective material 70,72. Any base or wave generator as described herein is suitable for use in the method 200.

In some embodiments, obtaining a multicomponent mixture 400 in block 202 can be performed either before the multicomponent mixture 400 is delivered into the separation device or after a first solution S1 and a second solution S2 are pumped into the separation device. For example, the first solution S1 comprising the at least one component 110 can be mixed with a second solution S2, such as a rejuvenation solution, a wash solution, or both, in a container outside of a separation system 100 to generate the multicomponent mixture 400. The multicomponent mixture 400 can then be pumped into the separation device. Alternatively, a first solution S1 comprising at least one component 110 and the second solution S2, e.g., wash solution, a rejuvenation solution, or both, can pumped individually into the separation device such that the multicomponent mixture 400 is formed or mixed within a mixing portion 53 of the separation channel 22, 52 at or near the first end 18 of the channel.

In block 206, the method can comprise generating an SBAW W such that a pressure node N associated with the SBAW is located within the separation channel 22, 52, and separates the at least one component 110 from the multicomponent mixture 400. Separating is physically performed by a pressure node N naturally accompanying the SBAW W. The pressure node forces, pushes, or moves the at least one component to a location within the separation channel. The separation channel can have a cross-sectional geometry designed to have distinct separation areas that promote separation, isolation and concentration of certain ones of the at least one component 110. In some examples, the separation channel 22, 52 can have a triangular cross-sectional geometry and, about midway through the separation channel, the separation channel can define a plurality of isolation channels 64, 66. In an example, the separation channel can define three triangular isolation channels 64 each having triangular cross-sectional geometries and positioned along a different one of the three corners of the separation channel, such that the isolation channels having a triangular cross-sectional geometry are not in contact with one another. In other examples, the separation channel and triangular isolation channels 64a, 64b, 64c can collectively define a central isolation channel 66 positioned centrally to the three triangular isolation channels. In some examples, the central isolation channel 66 can have a hexagonal cross-sectional geometry. In such examples, the method 200 can comprise delivering, such as by flowing or pumping, the multicomponent mixture 400 relative to at least one SBAW W. One or more pressure nodes N separate multiple components 122, 124, 126 of the at least one component 110, such as red blood cells 122, white blood cells 124, and platelets 126, from a solution 402 of the multicomponent mixture 400. The multiple components 122, 124, 126 can be isolated in the three triangular isolation channels 64a, 64b, 64c and the rest of the mixture 402 can flow through the central isolation channel 66.

The method 200 can comprise collecting one or more isolated components of the at least one component 110, as shown in block 208. Collecting can comprise collecting the at least one component 110 at the at least one outlet 30, 58, 60 of the separation device. In some embodiments, collecting the at least one component 110 can comprise coupling a fitting 75 into the at least one outlet of separation channel such that the at least one component 110 is collected separately from the rest of the multicomponent mixture 400, 402. For example, red blood cells 122 can be collected at the outlet 30 after they are separated from at least one of a rejuvenation solution or wash solution 402 by a pressure node N. Where multiple components are separated from the multicomponent mixture 400 in a separation device, such as a device having three isolation channels, the method can comprise collecting a different component 122, 124, 126 from each outlet 58a, 58b, 58c. For example, red blood cells 122, white blood cells 124, and platelets 126 can be individually isolated from the first, second, and third isolation channels 64a, 64b, 64c, respectively. Additionally, the rest of the multicomponent mixture, such as a solution 402, can be isolated from a central isolation channel 60. Fittings 75 can be coupled to each outlet 58, 60 to facilitate collecting. At the completion of the method 200, the isolated component(s) can be used, for example, in a medical procedure, such as a blood transfusion.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A separation device comprising a body having:
   a first surface and a second surface, generally opposing the first surface, the body defining a separation channel extending between a first end and a second end, the separation channel defining a plurality of isolation channels having a non-circular cross-sectional geometry transverse to a longitudinal axis of the separation channel.

2. The separation device of claim 1, wherein the plurality of isolation channels comprise at least three isolation channels.

3. The separation device of claim 1, wherein the body comprises a phantom material configured to mimic an acoustical property of water.

4. The separation device of claim 1, wherein the noncircular cross-sectional geometry of at least one of the plurality of isolation channels is a hexagon, a triangle, a triangle with rounded corners, a tear-drop shape, or a pinched tear-drop shape.

5. The separation device of claim 1, wherein the separation channel defines three isolation channels having triangular cross-sectional geometries, each of the three isolation channels positioned along a different corner or side of the separation channel.

6. A separation system for separating at least one component from a multicomponent mixture, the system comprising:
- a separation device comprising a body having a first surface and a second surface, opposing the first surface, the body defining a separation channel extending between a first end and a second end, wherein the separation channel defines a plurality of isolation channels having a non-circular cross-sectional geometry transverse to a longitudinal axis of the separation channel;
- a reflective material configured to reflect an acoustic wave; and
- a base comprising an interdigitated transducer (IDT),
- wherein in an assembled configuration the reflective material is positioned on the first surface and the separation device is positioned relative to the base such that the separation channel is positioned between the IDT and the reflective material.

7. The system of claim 6, wherein the separation device comprises a phantom material configured to mimic an acoustic property of a tissue.

8. The system of claim 6, wherein the base comprises a piezoelectric material.

9. The system of claim 6, wherein the separation device further comprises an inlet adjacent to the first end and a plurality of outlets, corresponding to the plurality of isolation channels, adjacent to the second end.

10. The system of claim 6, wherein the plurality of isolation channels have a cross-sectional size that increases between the first end and the second end.

11. The system of claim 6, wherein the separation device comprises a phantom material configured to have about the same water content as a tissue.

12. The system of claim 6, wherein the separation channel defines three isolation channels having triangular cross-sectional geometries, each of the three isolation channels positioned along a different corner or side of the separation channel.

13. The system of claim 6, wherein the isolation channels increase in size in a direction from the first end to the second end.

14. A separation device comprising:
- a body defining a separation channel extending between a first end and a second end, the separation channel including a plurality of isolation channels, at least one of the plurality of isolation channels having a non-circular cross-sectional geometry transverse to a longitudinal axis of the separation channel.

15. The separation device of claim 14, wherein the separation channel includes three isolation channels.

16. The separation device of claim 15, wherein each one of the three isolation channels is positioned along a different corner or side of the separation channel.

17. The separation device of claim 15, wherein at least one of the three isolation channels has a generally triangular cross-sectional geometry.

18. The separation device of claim 14, wherein the separation device comprises a phantom material configured to mimic an acoustic property of a tissue or an acoustic property of water.

19. The separation device of claim 14, wherein the plurality of isolation channels increases in size between the first end and the second end.

20. The separation device of claim 14, wherein the separation channel includes a plurality of outlets having a non-circular cross-sectional geometry transverse to the longitudinal axis.

* * * * *